US006537519B2

(12) United States Patent
Borel et al.

(10) Patent No.: US 6,537,519 B2

(45) Date of Patent: Mar. 25, 2003

(54) METHOD FOR THE PRODUCTION OF CONJUGATES AND USES THEREOF FOR THE PREVENTION AND TREATMENT OF ALLERGIC REACTIONS AND AUTOIMMUNE DISEASES

(75) Inventors: Yves Borel, Vandoeuvres (CH); Werner Schlegel, Chancy (CH); Erwin Gelfand, Englewood, CO (US)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/755,132

(22) Filed: Jan. 8, 2001

(65) Prior Publication Data

US 2001/0007755 A1 Jul. 12, 2001

(30) Foreign Application Priority Data

Jan. 11, 2000 (EP) .......................................... 00100461

(51) Int. Cl.[7] ........................ A61K 51/08; A61K 39/35; A61K 39/395; C07K 16/00; C07K 17/06

(52) U.S. Cl. .................. 424/1.49; 424/1.53; 424/178.1; 424/179.1; 424/275.1; 424/194.1; 530/387.1; 530/391.1; 530/391.5; 530/391.9

(58) Field of Search ........................... 530/391.1, 391.9, 530/391.5, 387.1, 350; 424/1.49, 1.53, 194.1, 178.1, 179.1, 275.1

(56) References Cited

FOREIGN PATENT DOCUMENTS

| | | | |
|---|---|---|---|
| DE | 40 14 540 | A1 | 11/1991 |
| EP | 0 367 166 | A1 | 5/1990 |
| WO | WO 89/11867 | A1 | 12/1989 |
| WO | WO 91/08773 | A1 | 6/1991 |

OTHER PUBLICATIONS

Voet et al., Biochemistry I, 1990, pp. 126–234.*

Ngo et al., 1994, The Protein Folding Problem and Tertiary Structure Prediction, pp. 492–495.*

Fasler et al., J. Allergy and Clinical Immunology 101(4 pt 1): 521–30, Apr. 1998.*

H.A. Sampson, *J. Allergy Clin. Immunol.* 78(1): 212–219 (1986).

R.E. Billingham et al., *Nature* 172(4379): 603–606 (1953).

J.W. Kappler et al., *Cell* 49: 273–280 (1987).

M.K. Jenkins & R.H. Schwartz, *J. Exp. Med.* 165: 302–319 (1987).

R.K. Gershon & K. Kondo, *Immunology* 21: 903–914 (1971).

M.A. Cremer et al., *J. Immunol.* 131(6): 2995–3000 (1983).

H.L. Weiner et al., *Annu. Rev. Immunol.* 12: 809–837 (1994).

W.Y. Lee & A.H. Sehon, *Nature* 267: 618–619 (1977).

D.H. Katz et al., *J. Exp. Med.* 134: 201–223 (1971).

A. Muckerheide et al., *J. Immunol.* 119(4): 1340–1345 (1977).

J.J. Machiels et al., *J. Clin. Invest.* 85: 1024–1035 (1990).

Y. Borel, in *Therapy of Autoimmune Diseases. Concepts in Immunopathology*, (J.M. Cruse & R.E. Lewis Jr., Eds.), 7: 145–161, Karger, Basel (1989).

A.H. Sehon, *Prog. Allergy* 32:161–202 (1982).

L.G. Fillion et al., *Cell Immunol.* 54: 115–128 (1980).

H. Borel & Y. Borel, *J. Immunological Methods* 126: 159–168 (1990).

Y. Borel et al. *J. Exp. Med.* 131: 603–610 (1970).

Y. Borel et al. *Annals New York Acad. of Sci.* 778: 80–87 (1996).

H. Tighe, et al. "Coupling of CpG Motif Immunostimulatory DNA to Ragweed Allergen amba 1 Induces a Th1 Response to Allergen" *Journal of Allergy and Clinical Immunology* 103(1):S48 (1999).

Monika Kroez, et al. "Therapy of Experimental Allerigic Encephalomyelitis in Rats with Wubcutaneous Immunoglobulins" *Journal of Autoimmunity* (No. Suppl.):94 (1999).

L.S. Barak, et al. "Internal trafficking and surface mobility of a functionally intact beta2–adrenergic receptor–green fluorescent protein conjugate" *Mol Pharmacol* 51(2): Abstract (1997).

X. Feng, et al. "Visualization of dynamic trafficking of a protein kinase C betaII/green fluorescent protein conjugate reveals differences in G protein–coupled receptor activation and desensitization" *J Biol Chem* 273(17): Abstract (1998).

D. Martinez–Fong, et al. "Neurotensin–SPDP–poly–L–lysine conjugate: a nonviral vector for targeted gene delivery to neural cells" *Brain Res Mol Brain Res* 69(2): Abstract (1999).

E. Ishikawa, et al. "Potential of the immune complex transfer enzyme immunoassay for antigens and antibodies to improve the sensitivity and its limitations" *J Clin Lab Anal* 12(3): Abstract (1998).

* cited by examiner

*Primary Examiner*—Christina Chan
*Assistant Examiner*—Phuong N. Huynh
(74) *Attorney, Agent, or Firm*—Finnegan, Henderson, Farabow, Garrett and Dunner, L.L.P.

(57) ABSTRACT

The present invention relates to a method for the preparation of a conjugate comprising a first and a second polypeptide, said method comprising the steps of (a) incubating said first polypeptide in the presence of a heterobifunctional crosslinker comprising an N-hydroxylsuccinimide ester group and a maleimide group linked via a polyethylene oxide spacer; (b) removing excess heterobifunctional crosslinker; and (c) incubating the reaction product of step (b) with said second polypeptide, wherein said second polypeptide comprises at least one sulfhydryl group.

Figure 1:
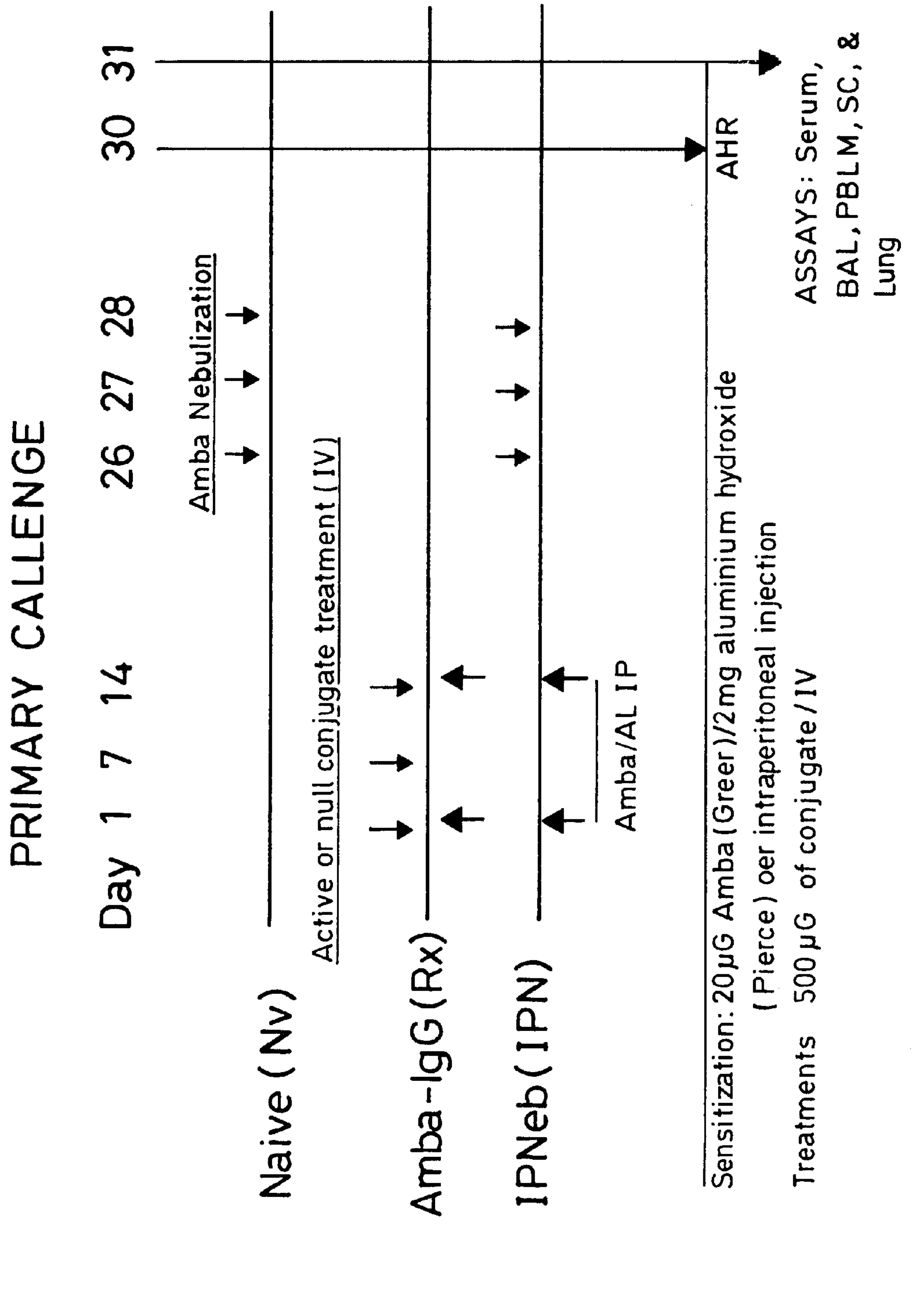

Furthermore, the present invention relates to a conjugate obtainable by the method of the present invention. Also described is a pharmaceutical composition comprising the conjugate of the present invention and, optionally, a pharmaceutically acceptable carrier and/or diluent, and the use of the conjugate for the preparation of a pharmaceutical composition for preventing and/or treating an allergic disease or an autoimmune disease.

13 Claims, 9 Drawing Sheets

Conjugate 2
IgG/Sulfo GMBS/AMBA-1(1/0,5 M/M) SATA

Immunoblot Anti-AMBA-1

IgG
AMBA-1
Conjugate 1
Conjugate 2

Effect of murine AMBA-IgG conjugates on airway hyperresponsiveness

Conjugate 1 IgG/C22H31N3O11/AMBA-1 (1/0.5M/M) SATA

Conjugate 2 IgG/Sulfo GMBS/AMBA-1 (1/0.5M/M) SATA

Effet of AMBA-IgG conjugate treatments on eosinophils in BALF

(Bar chart: Y-axis % from 0 to 8; X-axis categories: Nv, IPN, 1Rx, 2Rx; IPN ≈ 7.5, 2Rx ≈ 4.8)

Effet of AMBA-IgG treatments on serum AMBA-IgE

(Bar chart: Y-axis EU/ml from 0 to 800; X-axis categories: Nv, IPN, IgGRx1, IgGRx2; IPN ≈ 720, IgGRx2 ≈ 200)

EFFECT OF AMBA-IgG TREATMENTS ON AIRWAY HYPERRESPONSIVENESS

EFFECT OF AMBA-IgG TREATMENTS ON AIRWAY HYPERRESPONSIVENESS

Effect of AMBA-IgG conjugates on AHR following sensitization/challenges and before provocation

METHOD FOR THE PRODUCTION OF CONJUGATES AND USES THEREOF FOR THE PREVENTION AND TREATMENT OF ALLERGIC REACTIONS AND AUTOIMMUNE DISEASES

The present invention relates to a method for the preparation of a conjugate comprising a first and a second polypeptide, said method comprising the steps of (a) incubating said first polypeptide in the presence of a heterobifunctional crosslinker comprising an N-hydroxylsuccinimide ester group and a maleimide group linked via a polyethylene oxide spacer; (b) removing excess heterobifunctional crosslinker; and (c) incubating the reaction product of step (b) with said second polypeptide, wherein said second polypeptide comprises at least one sulfhydryl group. Furthermore, the present invention relates to a conjugate obtainable by the method of the present invention. Also described is a pharmaceutical composition comprising the conjugate of the present invention and, optionally, a pharmaceutically acceptable carrier and/or diluent, and the use of the conjugate for the preparation of a pharmaceutical composition for preventing and/or treating an allergic disease or an autoimmune disease.

Immunologic tolerance may be defined as a state of antigen-specific unresponsiveness induced by preexposure to an antigen. If the antigen is an allergen, the immune response is defined as allergy, an adverse reaction with an immunologic basis mediated by IgE immunoglobulin (Sampson (1986), J. Allergy Clin. Immunol. 78:212–219). The immune system may also be a cause of disease or other undesirable consequences, when the principle of self/non-self recognition breaks down and the body's own components are recognized as non-self (autoantigens) in which case autoimmune diseases can ensue.

Interest in immunologic tolerance, discovered by Medawar almost half a century ago (Billingham et al. (1953), Nature 172:603–606), has increased for two main reasons: (1) Several of its mechanisms, such as clonal deletion (Kappler et al. (1987), Cell 49:273–280), anergy (Jenkins and Schwartz (1987), J. Exp. Med. 165:302–319), and regulatory T cells (Gershon and Kondo (1971), Immunology 21:903–914) have been uncovered. (2) Both systemic and oral tolerance (Cremer et al. (1983), J. Immunol. 131:2995–3000; Weiner et al. (1994), Ann. Rev. Immunol. 12:809–837) can be induced to, it is hoped, prevent either autoimmune or allergic diseases. For example, several strategies have been used in trying to prevent allergy, including administration of modified allergen (Lee and Sehon (1977), Nature 267:618–649), allergen linked to nonimmunogenic carriers (Katz et al. (1971), J. Exp. Med. 134:201–203), single peptides (Muckerheide et al. (1977), J. Immunol. 119:1340–1345), or an allergen-antibody complex (Machiels et al. (1990), J. Clin. Invest. 85:1024–1035).

It is known that antigen presentation can influence the type of immune response. Not only haptens (Borel (1989), in "Concepts in Immunopathology", Cruse and Lewis (Eds.), 7:145–161, Karger, Basel; Sehon (1982), Prog. Allergy 32:161–202) but also proteins covalently linked to a carrier molecule naturally tolerated by the host, such as isologous immunoglobulin, can induce unresponsiveness to these proteins (Filion et al. (1980), Cell Immunol. 54:115–128; Borel and Borel (1990), J. Immunol. Methods 126:159–168).

However, although the above strategies proved to be partially successful, there is still a need for allergen and/or auto-antigen comprising conjugates with improved therapeutic properties.

Thus, the technical problem underlying the present invention was to provide a method for the production of such allergen and/or auto-antigen comprising conjugates.

The solution to this technical problem is achieved by providing the embodiments characterized in the claims.

Accordingly, the present invention relates to a method for the preparation of a conjugate comprising a first and a second polypeptide, said method comprising the steps of:

(a) incubating said first polypeptide in the presence of a heterobifunctional crosslinker comprising an N-hydroxylsuccinimide ester group and a maleimide group linked via a polyethylene oxide spacer;

(b) removing excess heterobifunctional crosslinker; and (c) incubating the reaction product of step (b) with said second polypeptide, wherein said second polypeptide comprises at least one sulfhydryl group.

It is envisaged in accordance with the present invention that the polyethylene oxide spacer may consist of from 1 to 10 monomer units. Preferably, the spacer consists of from 2 to 5 monomer units.

Unexpectedly, it has been found in accordance with the present invention that due to the crosslinker used conjugates prepared by the method of the present invention show superior features as compared to conjugates prepared by prior art methods. For example, conjugates of ragweed derived antigen (Amba-l) and mouse IgG were prepared by the method of the present invention and a method using as crosslinker N-(γ-maleimidobutyroxy)sulfosuccimimide ester (sulfo-GMBS) a preferred prior art crosslinker (see Example 1, infra). The effects of both conjugates in the treatment of an allergic reaction to ragweed derived antigen were investigated. Surprisingly, it was found that the conjugate of the present invention leads to a significant reduction in airway hyperresponsiveness whereas the prior art conjugate has almost no effect when compared to sensitized animals (see Example 5 and FIG. 3). Furthermore, the conjugate of the present invention virtually eliminated eosinophils in the bronchoalveolar lavage fluid (BALF). This phenomenon was accompanied by a total suppression of specific anti-Amba-l IgE. In contrast, the prior art conjugate only moderately reduced eosinophils, and specific anti-Amba-l IgEs were only partially suppressed (see Example 5 and FIG. 4). These results clearly demonstrate that due to the crosslinker used the method of the present invention allows the person skilled in the art to produce conjugates with advantageous immunological properties which render these conjugates for instance suitable for the downregulation of the inflammatory and immunologic reactions of an allergic response.

In a preferred embodiment of the present invention, said at least one sulfhydryl group of said second polypeptide is introduced by:

(i) incubating said second polypeptide in the presence of N-succinimidyl-S-acetylthioacetate (SATA);

(ii) removing excess SATA;

(iii) incubating the reaction product of step (ii) in the presence of hydroxylamine; and (iv) removing excess hydroxylamine and acetylated hydroxylamine.

This embodiment is of particular importance in cases where said second polypeptide does not comprise at least one endogenous sulfhydryl group that is, for example, provided by a cysteine residue in the amino acid sequence, and which is suitable for crosslinking said second polypeptide with said first polypeptide via a disulfide bond. Sulfhydryl groups that are not suitable for crosslinking may be, for example, sulfhydryl groups that are not readily accessible for the sulfhydryl group of said first polypeptide due to the three dimensional conformation of said second polypeptide, or that are not available due to inter- or intramolecular disulfide bonds. Whether said second polypeptide comprises one or more sulfhydryl groups that allow effective crosslinking to occur or whether sulfhydryl groups have to be introduced into said second polypeptide can be determined by the person skilled in the art without further ado. For example, two polypeptides may be crosslinked by the method of the present invention and the quality and quantity of the obtained conjugate may be analyzed by SDS polyacrylamide gel electrophoresis under non-reducing conditions and immunoblotting with an antibody specific for one of the two crosslinked polypeptides. Preferably, the identity of the conjugate is verified with a second antibody specific for the second of the two polypeptides. For a detailed description of the above outlined experiment, reference is made to Example 1. If the results show that the quality and quantity of the conjugate is not satisfactory as compared to a reference conjugate like, for example, the IgG/Amba-l conjugate produced in Example 1, sulfhydryl groups may be introduced as described above.

In another preferred embodiment, said heterobifunctional crosslinker comprising an N-hydroxylsuccinimide ester group and a maleimide group linked via a polyethylene oxide spacer has the formula:

As discussed above, the method of the present invention may be, inter alia, used to produce conjugates that, if comprising an allergen, may be used as a “tolerogen”, i.e. as a conjugate capable of inducing immunologic tolerance in a subject allergic to the allergen it comprises. Without wanting to be bound to a specific scientific theory, it is envisaged that these tolerogenic properties are conferred to the conjugate by a molecule that is also comprised by the conjugate, and is recognized by the subject as “self” like, for example, an isologous or autologous immunoglobulin. Accordingly, the term “structurally equivalent fragment” as used in accordance with the present invention denotes fragments that show the same immunological properties as the entire immunoglobulin, i.e. that do not induce an immune response in the subject. Such a fragment may be, for instance, the Fc portion of an immunoglobulin.

In a more preferred embodiment, said immunoglobulin or structurally equivalent fragment thereof is an immunoglobulin G or a structurally equivalent fragment thereof.

In yet another preferred embodiment, said second polypeptide is an allergen, an autoantigen or an immunologically equivalent fragment of said allergen or autoantigen.

“Immunologically equivalent fragment” as used in accordance with the present invention denotes a fragment of an allergen or autoantigen that is capable of inducing the same

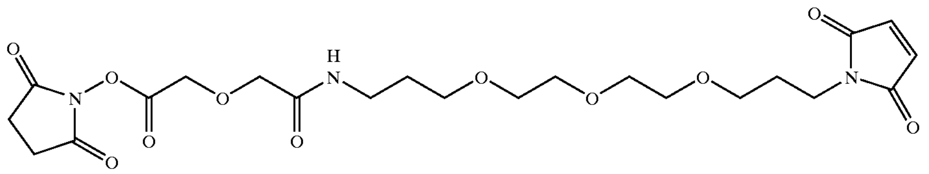

immune response in a subject as the corresponding allergen or autoantigen, i.e. the same allergic or autoantigenic reaction.

In a further preferred embodiment of the method of the present invention, the heterobifunctional crosslinker is used in step (a) in a 5- to 50-fold higher molar concentration than said first polypeptide.

In yet another preferred embodiment, steps (a) and (c) are performed in a temperature range from 20° C. to 37° C.

In a still further preferred embodiment, steps (a) and (c) are performed in a time range from 30 min to 120 min.

In another preferred embodiment of the method of the present invention, steps (a) and (c) are performed in a pH range from 7.0 to 9.0.

In a further preferred embodiment, the molar ratio of said first and second polypeptide is between 1:1 and 1:10.

In a more preferred embodiment of the method of the present invention, steps (a) and (c) are performed in a buffer comprising 0.15 M borate, pH 8.0 at 37° C. for 30 min, the heterobifunctional crosslinker is used in a 30-fold higher molar concentration than said first polypeptide, and the molar ratio of said first and second polypeptide is 1:10.

These conditions could be shown in accordance with the present invention to result in conjugates that are most effective and beneficial if used, for example, to counteract allergic reactions.

In another preferred embodiment, the method of the present invention further comprises the step of removing aggregated conjugate and providing the conjugate in monomeric form.

Unexpectedly, this step even further improves the properties of the conjugates of the present invention.

In a still further preferred embodiment, said first polypeptide is an immunoglobulin or a structurally equivalent fragment thereof.

Since it could be shown that conjugates comprising an immunoglobulin and, for example, an allergen induce unresponsiveness in a subject allergic to said allergen, it is envisaged in accordance with the present invention that conjugates comprising an immunoglobulin and, for example, an autoantigen can be used to induce unresponsiveness to said autoantigen and, thus, be used prophylactically in subjects suspected to have a predisposition for the development of the corresponding autoimmune disease.

In a more preferred embodiment said allergen is derived from ragweed, birch pollen, peanut, house dust mite, animal danders, mould, or is tropomyosin or an immunologically equivalent fragment thereof.

In another more preferred embodiment, said autoantigen is acetylcholine receptor, insulin, insulin receptor, myelin basic protein or an immunologically equivalent fragment of these proteins.

In another embodiment, the present invention relates to a conjugate obtainable by the method of the present invention.

As could be shown in accordance with the present invention, the conjugates of the invention do not only protect subjects against hypersensitivity type I reactions and, thus, the development of allergy. The conjugates of the inventions are also effective in downregulating allergic reactions and, thus, may be used to treat allergic diseases. Likewise, it is envisaged that conjugates comprising an immunoglobulin and, for example, an autoantigen may be used to ameliorate and/or treat the corresponding autoimmune disease and/or symptoms associated therewith.

The present invention also relates to a pharmaceutical composition comprising the conjugate of the present invention and, optionally, a pharmaceutically acceptable carrier and/or diluent.

Examples of suitable pharmaceutical carriers are well known in the art and include saline solutions, water, emulsions, such as oil/water emulsions, sterile solutions etc. Compositions comprising such carriers can be formulated by well known conventional methods. These pharmaceutical compositions can be administered to the subject at a suitable dose. Administration of the suitable compositions may be effected orally or parenterally, e.g., by intravenous, intraperitoneal, subcutaneous, intramuscular, topical, intradermal, intranasal or intrabronchial administration, or directly to the target site, e.g., by biolistic delivery to an internal or external target site or by catheter to a site in an artery. The dosage regimen will be determined by the attending physician and clinical factors. As is well known in the medical arts, dosages for any one patient depends upon many factors, including the patient's size and weight, body surface area, age, the particular compound to be administered, sex, time and route of administration, general health, and other drugs being administered concurrently. A typical dose can be, for example, in the range of 0.001 to 1000 μg. However, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Furthermore, the present invention relates to the use of the conjugate of the present invention for the preparation of a pharmaceutical composition for preventing and/or treating an allergic disease or an autoimmune disease.

In a preferred embodiment of the use of the present invention, wherein said allergic disease is an allergic reaction against an allergen derived from ragweed, birch pollen, peanut, house dust mite, animal danders, mould, or tropomyosin or an immunologically equivalent fragment thereof.

In another preferred embodiment, said autoimmune disease is Myasthenia gravis, type I Diabetes or multiple sclerosis.

The Figures show:

FIG. 1: Primary challenge protocol. Mice were sensitized to Amba-1 (ragweed extract) together with alum on days 1 and 14 and subsequently challenged with aerosolized (nebulized) Amba-1 on days 26, 27 and 28. Naïve (Nu) animals received no sensitization. IPNeb: intraperitoneal sensitization/airway nebulization; Amba/AL: Amba-1/alum; AHR: airway hyperresponsiveness; BAL: bronchoalveaolar lavage; PBLN: peribronchial lymph nodes; SC: spleen cells.

Figure 2A:
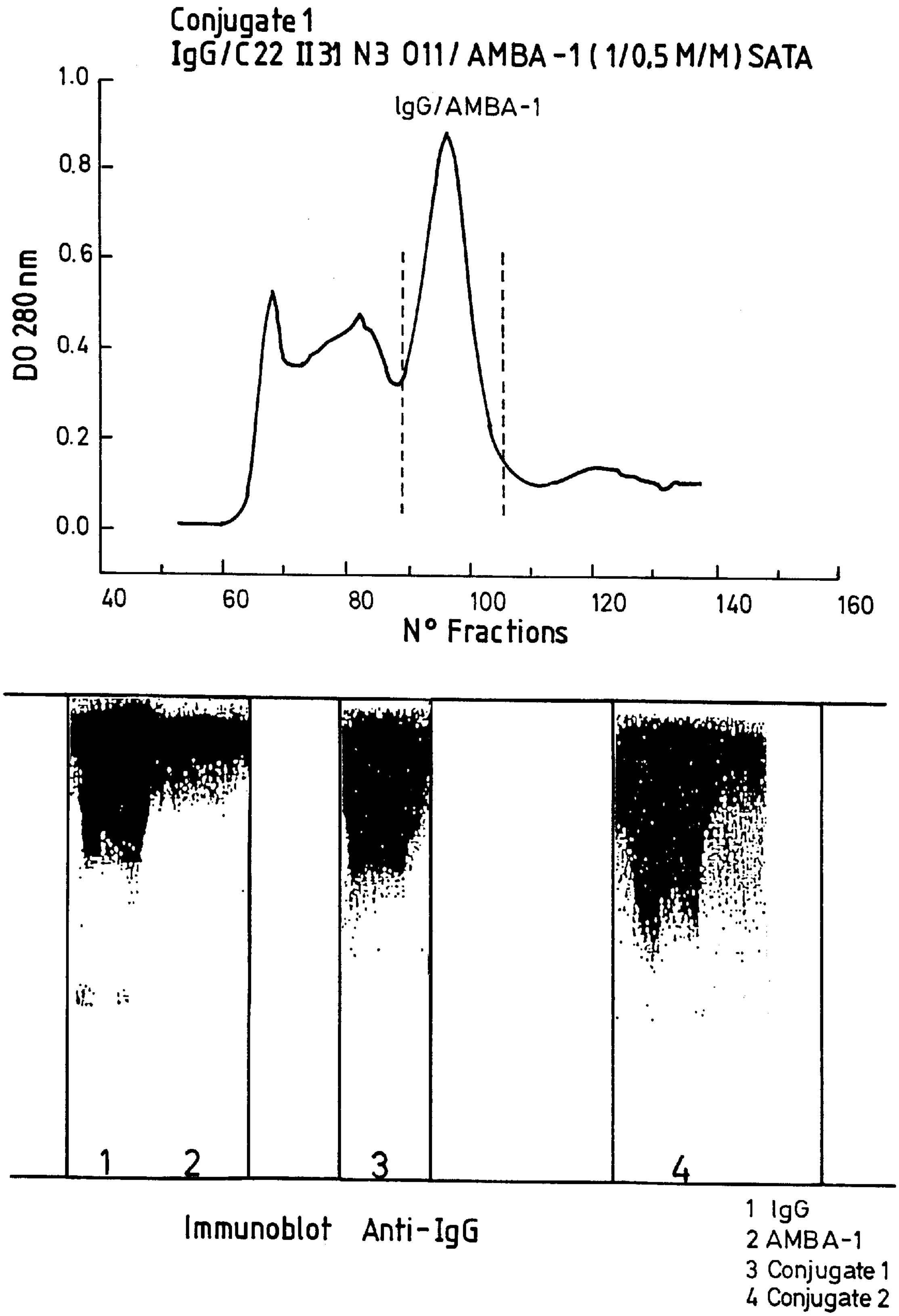
Figure 2B:
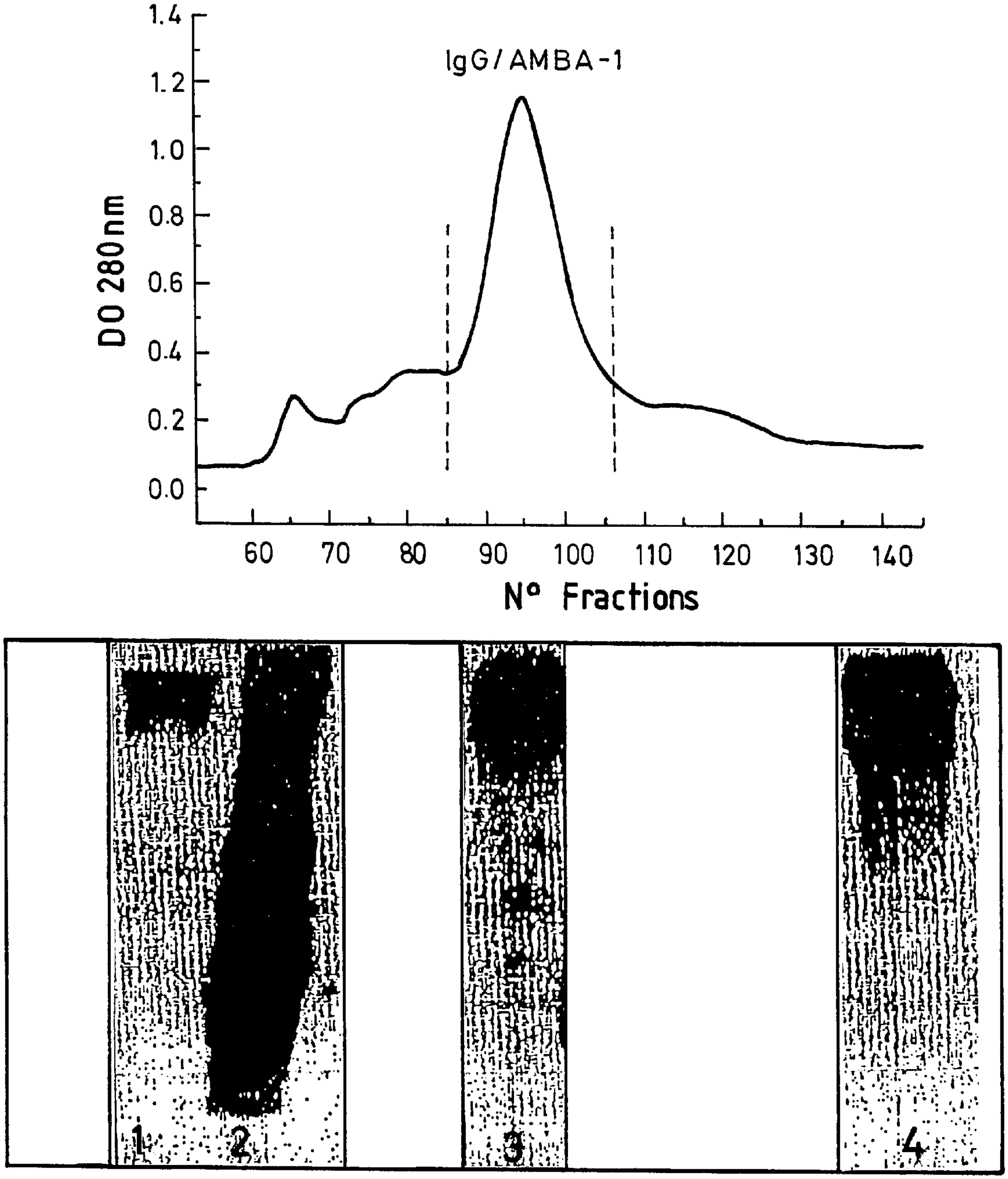

FIGS. 2*a–b*: Chromatography (top) and western blots (bottom) of the conjugates (a) conjugate 1 and (b) conjugate 2.

Figure 3:
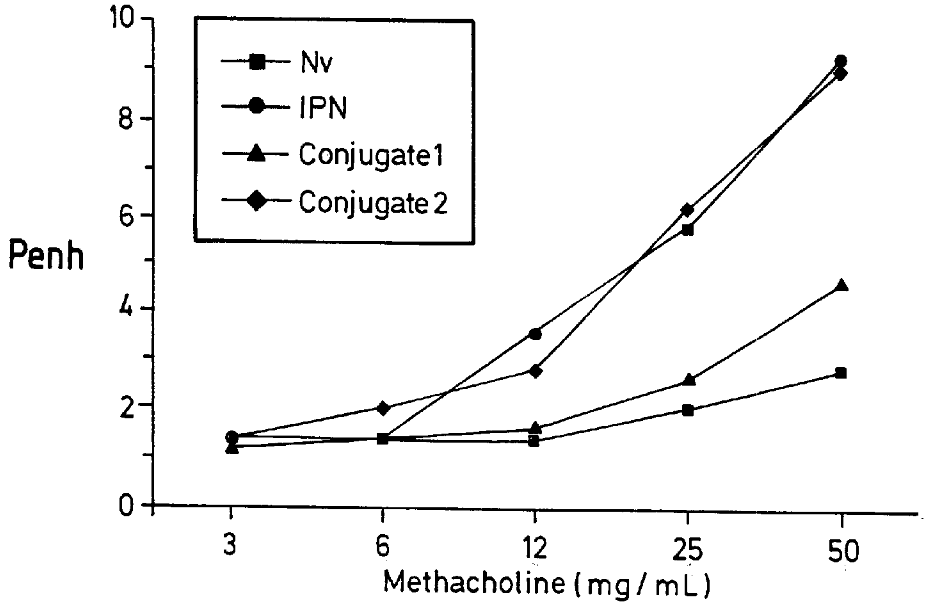

FIG. 3: Effect of conjugates on airway function. Penh: enhanced pause—a measure of airway function.

Figure 4A:
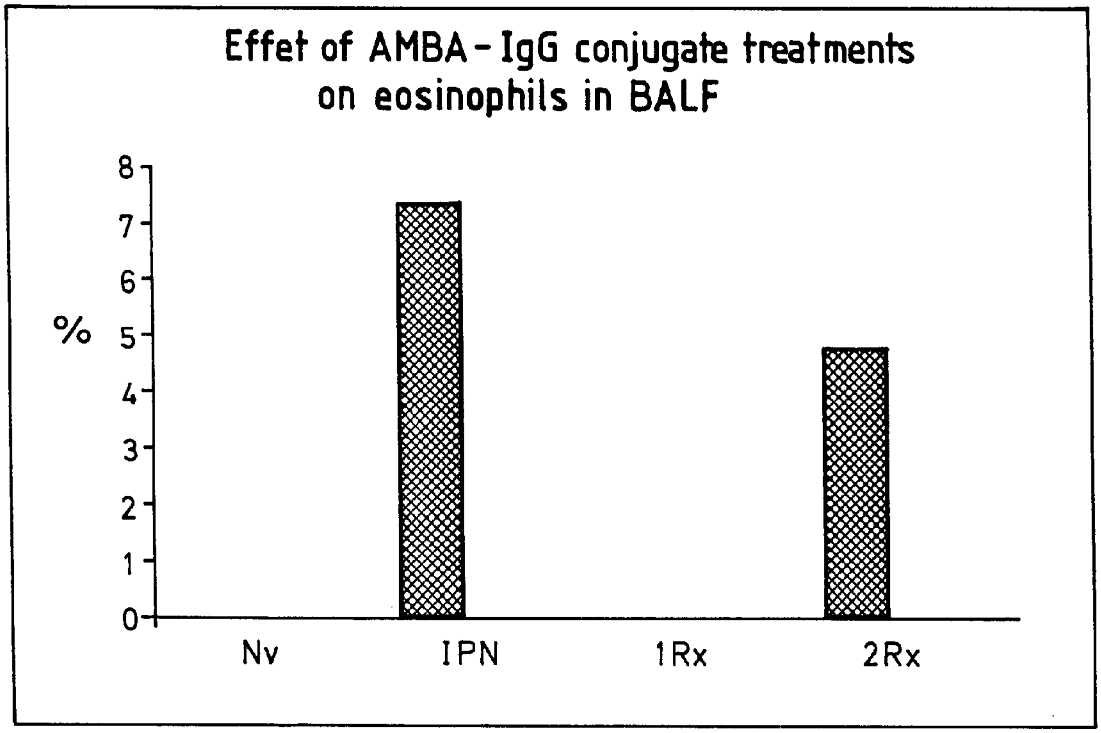
Figure 4B:
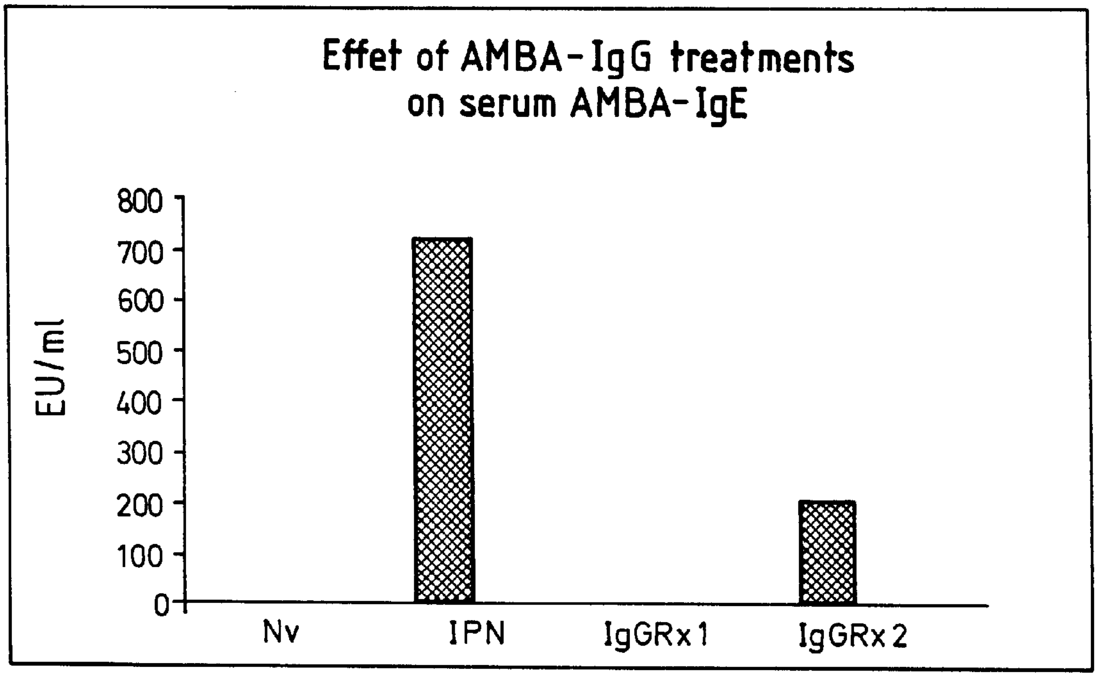

FIGS. 4*a–b*: Effect of conjugates on eosinophil infiltration in the bronchoalveolar lavage fluid (BALF)(a) and serum antigen-specific IgE levels(b). EU/ml: Elisa units/ml.

Figure 5:
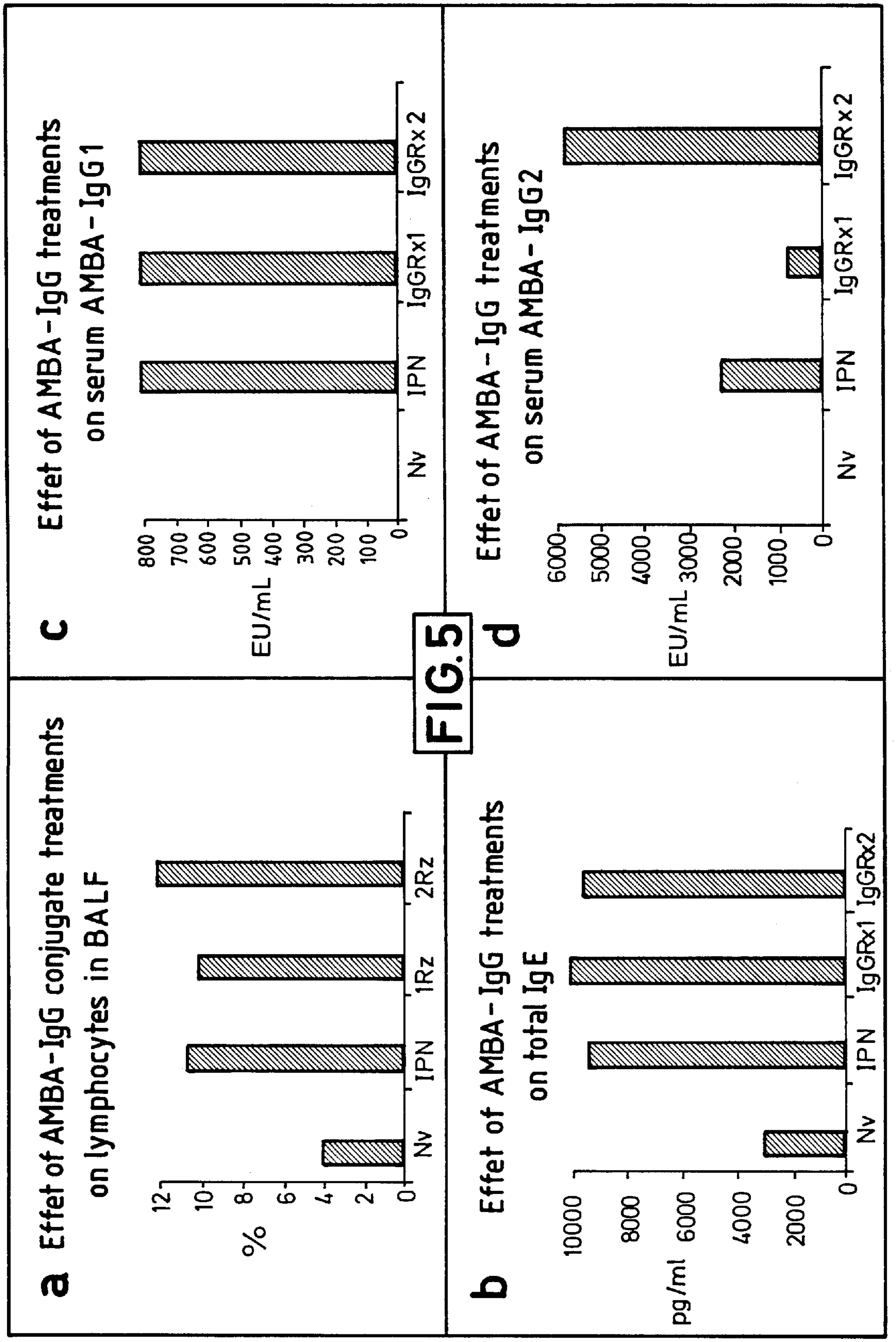

FIG. 5: Effect of conjugates on BALF lymphocyte numbers(a), total IgE(b) and serum levels of antigen-specific IgG1(c) and IgG2(d).

Figure 6:
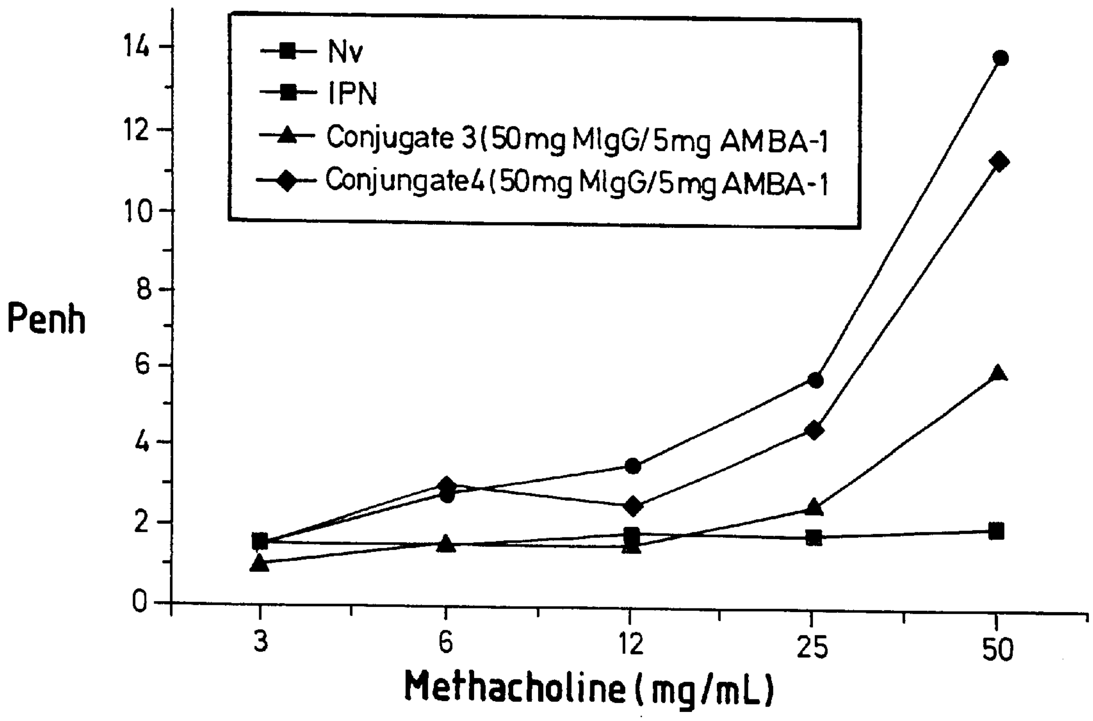
Figure 6:
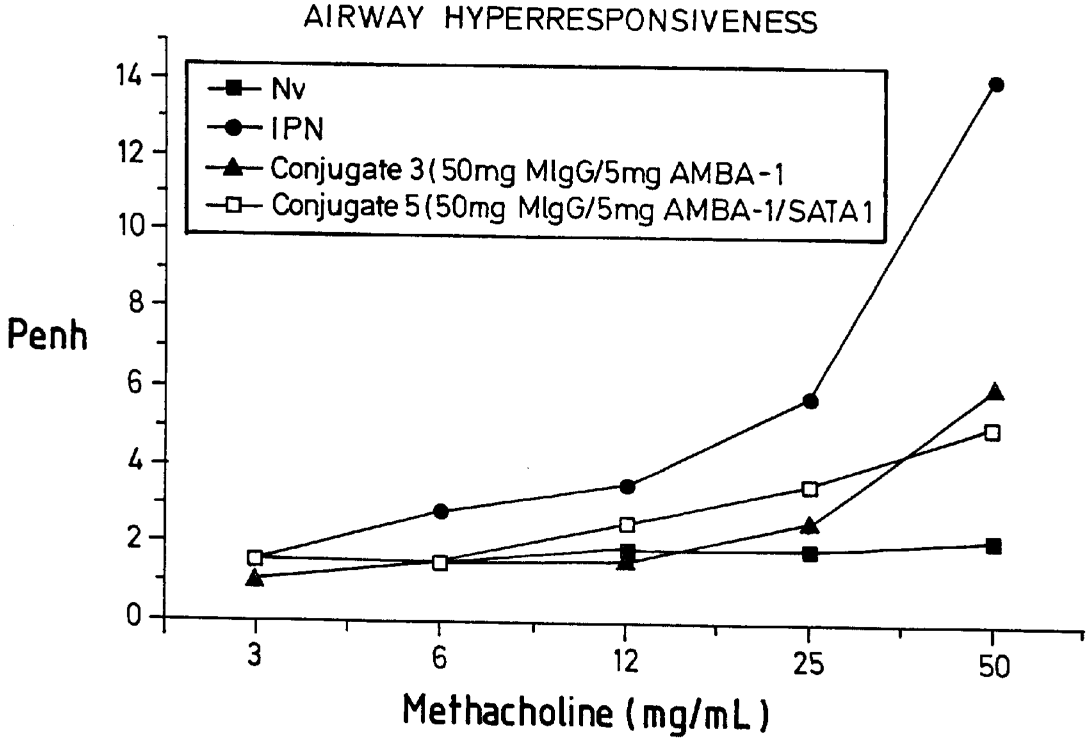

FIG. 6: Effect of different conjugates on airway function.

Figure 7:
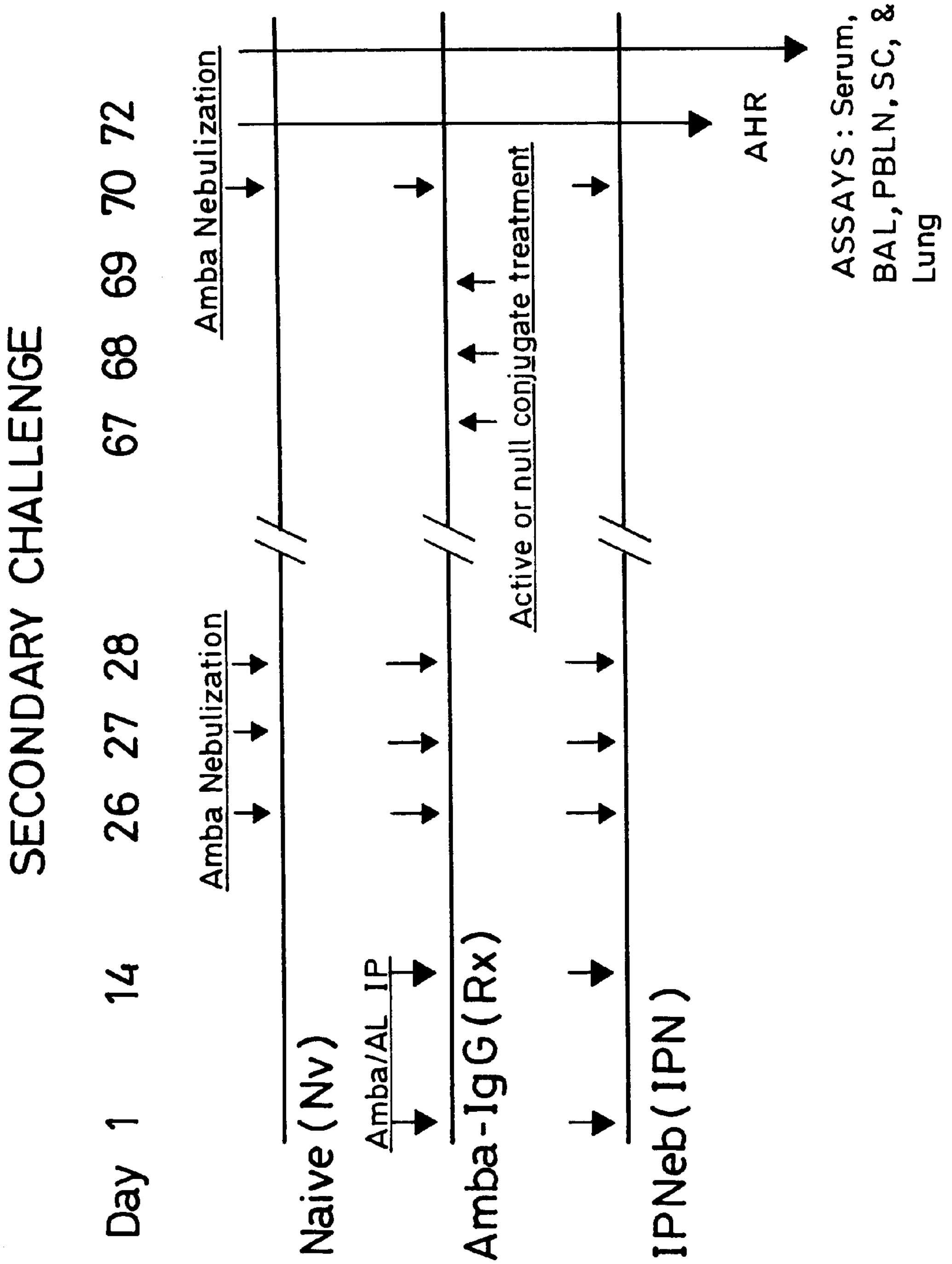

FIG. 7: Secondary challenge protocol.

Figure 8:
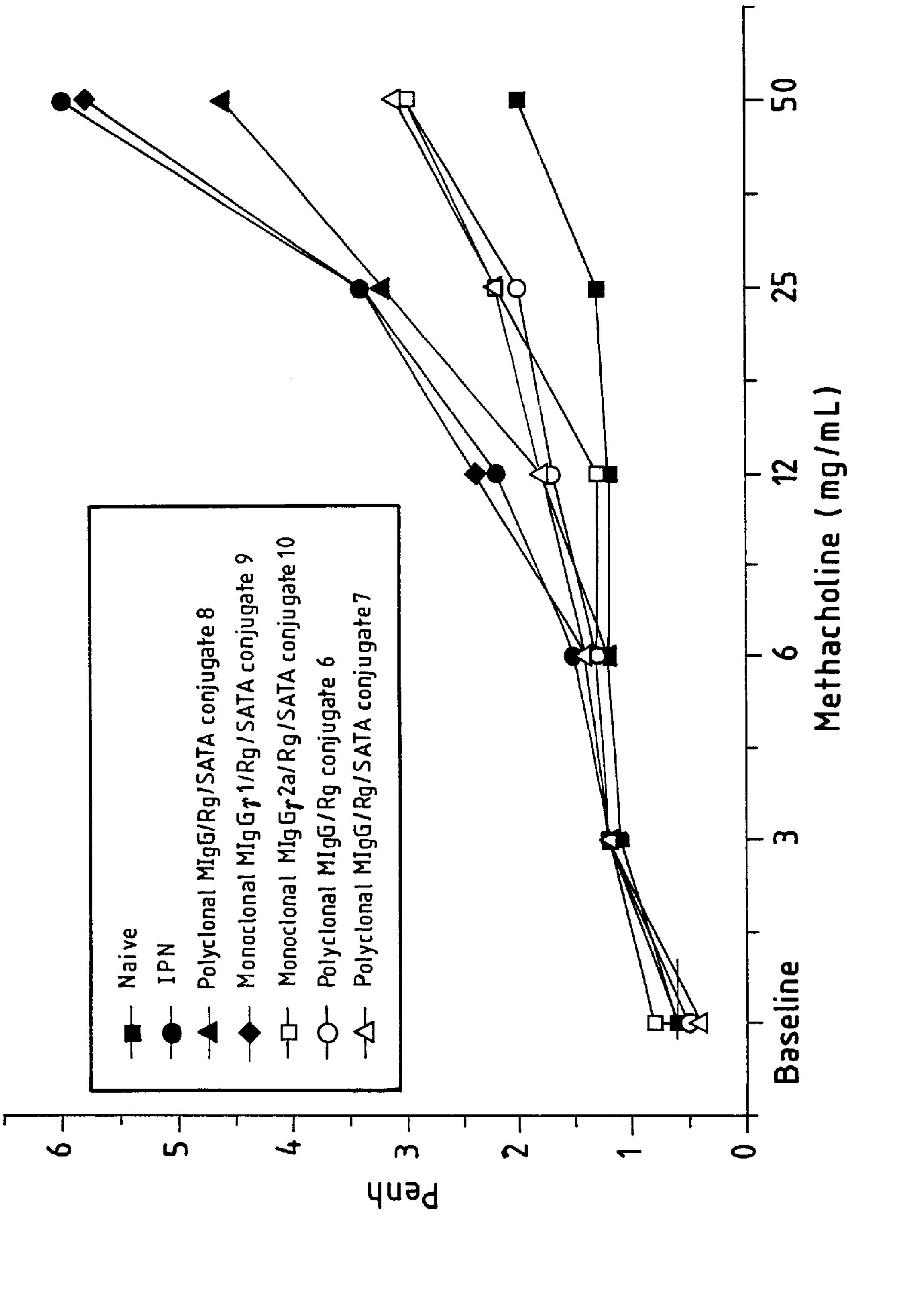

FIG. 8: Effect of different conjugates on airway function after secondary challenge.

The Examples illustrate the invention.

EXAMPLE 1

Preparation of a mouse IqG/Amba-l conjugate with either $C_{22}H_{31}N_3O_{11}$ or sulfo-GMBS 50 mg of mouse IgG (purchased from Prof. Ptak, Gracow Poland) were dissolved in 5 ml of 0.15 M borate buffer, pH 8.0. 100 μl of $C_{22}H_{31}N_3O_{11}$ crosslinker were added at a concentration of 97 mM in ethanol, and the sample was mixed gently for 1 hr at room temperature. When sulfo-GMBS was used instead of $C_{22}H_{31}N_3O_{11}$, 150 μl of sulfo-GMBS at a concentration of 9 mM in $H_2O$ were added to 50 mg of mouse IgG in 5 ml 0.15 M borate buffer, pH 8.0 for 30 min at 37° C. Immediately thereafter excess crosslinker was removed by gel filtration using a G25 Sephadex column in 0.15 M borate buffer pH 7.5 with 10 mM EDTA. The fractions containing the protein peak were collected and reduced to a volume of 3 ml.

At this point, the maleimide-activated protein may be used immediately in a conjugation reaction with a sulfhydryl-containing protein. If free SH groups are not available, SATA reagent can be added on the allergen.

To do so, 4.8 mg of Amba-l (purified ragweed purchased from Greer laboratory) were dissolved in borate buffer. 50 μl of SATA, 65 mM in DMSO were added, and the reaction mixture was incubated at room temperature for 30 minutes. Excess SATA was removed by gel filtration on a Sephadex G25 column in 0.15 M borate buffer pH 7.5 with 10 mM EDTA. Fractions containing Amba-l modified with SATA were collected and concentrated in 6 ml. 600 μl of hydroxylamine, 0.5 M in borate buffer, 10 mM EDTA were added to 6 ml Amba-l/SATA, and incubated for 2 hr at room temperature with constant mixing. Excess hydroxylamine was removed on a G25 Sephadex column in 0.15 M borate buffer, 10 mM EDTA, pH 7.5. Fractions containing Amba-l modified with SATA and hydroxylamine were collected and concentrated in 5 ml.

Mouse IgG (3 ml) and modified Amba-l (5 ml) were mixed and incubated for 30 minutes at 37° C. with constant mixing. The mouse IgG/Amba-l conjugate was filtered before chromatography on a Sephacryl-S 300 HR in 0.15 M borate buffer, $NaN_3$ 0.05%, pH 8.0, degassed under vacuum at 4° C. The fractions containing the conjugate were pooled and, after dialysis against 0.15 M NaCl, were concentrated in 4 ml (about 4 mg/ml).

If activation of the allergen with SATA is omitted, mouse IgG/$C_{22}H_{31}N_3O_{11}$ is mixed directly with 5 mg of Amba-l for 2 hr at room temperature and then for 30 minutes at 37° C. with constant mixing. Then the conjugate is filtered and chromatographed on Sephacryl-S 300 HR as described above.

In each case, successful conjugation was verified by 8% polyacrylamide gel electroporesis and immunoblotting with specific antibodies (i.e. anti-IgG and anti-ragweed).

EXAMPLE 2

Sensitization and challenge

On days 1 and 14, Balb/c mice received intraperitoneal injections of 20 μg Amba-l peptide (Greer Laboratories) together with 2 mg aluminium hydroxide (Pierce). On day 26, 27 and 28 mice were exposed to a 20 minutes aerosolization with a 0.2% solution of Amba-l in a closed plastic box. Airway responsiveness was assessed 48 hours after the last challenge by barometric plethysmography using whole body plethysmography (WBP) (Buxco, Troy, N.Y.) in live, unrestrained and non-ventilated mice in response to inhaled methacholine (Mch) in a dose-response manner. Before taking readings, the box was calibrated with a rapid injection of 150 μl air into the main chamber. Measured were pressure differences between the main chamber of the WBP, containing the animal, and a reference chamber. A pneumotachograph with defined resistance in the wall of the main chamber allows the measurement of flow (boxflow, pseudoflow) in and out of the main chamber. The measured box flow correlates in normal animals with the animal's flow and permits in non-bronchial constricted conditions the determination of tidal volumes and flow amplitudes (pseudovolume, pseudoflow) from box pressure signals. In contrast to the original closed Fenn box, WBP uses a pneumotachograph in the wall. Thus, the box pressure signal reflects box flow changes due to respiration rather than box volume changes due to respiration, but still allows for determination of tidal volumes using the Fenn formula.

Inspiration and expiration are recorded by establishing start-inspiration and end-inspiration as the box pressure curve crosses the zero point. Start of an inspiration is determined by extrapolating from a straight line drawn from two levels the rising inspiratory box flow. In a pilot experiment, a non-bronchial constricted, conscious mouse was placed within a head-out body plethysmograph sealed with a latex collar and then placed into the current WBP. Comparison of the thoracic flow signal with the WBP flow signal showed a nearly identical wave form with a slight (<10 ms) delay of start-inspiration of the WBP signal and congruency of end-inspiration (personal communication, M. Lomask, Buxco). Time of inspiration (Ti) is defined as the time from the start of inspiration to the end of inspiration; time of expiration (Te) as the time from the end of inspiration to the start of the next inspiration. The maximum box flow occurring during one breath in a negative or positive direction is defined as peak inspiratory flow (PIF) or peak expiratory flow (PEF), respectively. Recordings of every ten breaths are extrapolated to define the respiratory rate in breaths per min. The relaxation time (Tr) is defined as the time of volume decay of the pseudo-expiratory volume (area under the box flow waveform in expiration) to 36%. This may thus serve as a correlate to the time constant (RC) of the decay of the volume signal to 36% of the peak volume in passive expiration. During bronchoconstriction, the main alteration occurs during early expiration and leads to changes in the waveform of the box pressure signal. This change in the waveform can be quantified comparing the mean expiratory box flow during early expiration (MF1) with the mean expiratory box flow during late expiration (MF2) by measurement of Pause, with:

MF1=mean pseudoflow 1

MF2=mean pseudoflow 2

V=pseudo-expiratory volume

MF1=0.65 V/Tr

MF2=0.35 V Te−Tr

Pause=Te−Tr/Tr−0.35 V/0.65 V×MF1/MF2−MF1/MF2

During bronchoconstriction, the changes in box flow during expiration (PEF) are more pronounced than during inspiration (PIF). This is reflected by the formula for enhanced Pause (Penh), a dimensionless value used in this paper to empirically monitor airway function:

Penh=Pause×PEF/PIF

Penh reflects changes in the box flow waveform from both inspiration and expiration (PIF, PEF) and combines it with the comparison of early and late expiratory box flow (Pause). Penh is not a function of the absolute box flow amplitude or the respiratory rate, but rather of the proportion of inspiratory to expiratory flow and of the timing of expiration.

Mice were placed in the main chamber and baseline readings were taken and averaged for three minutes. Aerosolized PBS or methacholine in increasing concentrations (3 to 50 mg/ml) were nebulized through an inlet of the main chamber for three minutes and readings were taken and averaged for three min following each nebulization. Airway reactivity was expressed as a fold increase for each concentration of MCh ($Penh_{MCh}$) compared to Penh values after PBS challenge ($Penh_{PBS}$).

For the quantification of the dose-response to methacholine, the linear regression of Penh on log base 2 was calculated for individual mice. The log dose corresponding to an increase in Penh of 100% or 200%, respectively, was determined and the average log doses of the different groups were compared by analysis of variance. The data are reported as the geometrical mean with the lower and upper limit of the 95% confidence interval.

Conjugates were given intravenously on days 1, 7 and 14 at a dose of 500 μg.

Serum was obtained 48 hours after the last challenge (after airway function is assessed) and total IgE and antigen specific IgE, IgG1, IgG2 were measured by ELISA. Bronchoalveolar lavage fluid (BALF) was collected after measurements of airway function and eosinophil numbers as well as total lymphocyte counts were determined. A summary of a typical experimental protocol is presented in FIG. 1. Each group consisted of 5 to 6 animals.

EXAMPLE 3

Bronchoalveolar lavage (BAL), lung cell isolation

Lungs were lavaged via a tracheal tube with Hank's balanced salt solution (HBSS, 3×0.5 ml) and the cells in the lavage fluid were counted. Cells from BAL or lungs were resuspended in HBSS and counted with a hemocytometer. Cytospin slides were stained with Leukostat (Fisher Diagnostics) and differentiated in a blinded fashion by counting at least 300 cells by light microscopy.

EXAMPLE 4

Measurement of anti-OVA antibody and total Ig levels

Anti-Amba-1 Ig serum levels were measured by ELISA. The antibody titers of the samples were related to pooled standards that were generated in the laboratory and expressed as ELISA units per ml (EU/ml). Total IgE and IgG levels were determined using the same method compared with known mouse IgE or IgG standards (PharMingen, San Diego, Calif.). The limits of detection were 100 pg/ml for IgE and 1 ng/ml for IgG.

EXAMPLE 5

Comparison of $C_{22}H_{31}N_3O_{11}$ conjugates with sulfo-GMBS conjugates

Profile 1 and Profile 2 of FIG. 2 represent the elution profiles obtained by chromatography of the $C_{22}H_{31}N_3O_{11}$ conjugate (conjugate 1) and the sulfo-GMBS conjugate (conjugate 2), respectively. In both cases the conjugates react with either anti-IgG or anti-ragweed demonstrating the covalent binding of Amba-l to mouse IgG as seen on immunoblots.

Administration of conjugate 1 and 2 has a markedly different influence on airway function. Conjugate 1 leads to a significant reduction of airway function whereas conjugate 2 has almost no effect when compared to sensitized animals (positive control) (see FIG. 3). Likewise, conjugate 1 virtually eliminated eosinophils in BALF. This was accompanied by a total suppression of specific anti Amba-l IgE (FIG. 4). As expected, total IgE was unaffected by treatment as well as total lymphocyte count. There was a difference as far as specific IgG1 and IgG2 is concerned. Administration of either conjugate 1 or 2 resulted in an increase of IgG1 anti-Amba-l antibodies. In contrast, conjugate 1 appears to reduce anti IgG2 antibodies as in comparison to conjugate 2 (FIG. 5).

The increase in the IgG1 specific isotype in contrast to the decrease in IgG2 following administration of the conjugate is interesting. It could be due to several factors: (a) the dose of the conjugate, the animal species, a difference in susceptibility of the various immune responses following administration of tolerogen. A phenomenon reminiscent of what has been referred to as "immune deviation" or "split tolerance"; Borel et al., J. Exp. Med 131 (1970), 603; (b) whether suppression of all immune responses as shown for both cellular and humoral immunity; Borel et al., Parenteral and oral administration of Tolerogens i.e. Protein IgG conjugates, Proc. N.Y. Acad. of Sci. 778 (1996), 80–87; or whether the formation of IgG1 specific "blocking" antibody would be desirable to downregulate allergic reactions remains to be determined.

polyclonal IgG. The results demonstrate that while polyclonal IgG (conjugate 8) shows partial suppression, $\gamma_1$ (conjugate 9) was ineffective. In contrast, $\gamma_{2a}$ (conjugate 10) downregulates airway responsiveness in atopic asthma.

We claim:

1. A method for the preparation of a conjugate comprising an immunoglobulin or a structurally equivalent fragment thereof and an allergen or autoantigen, said method comprising the steps of:

(a) incubating said immunoglobulin or said structurally equivalent fragment thereof in the presence of a heterobifunctional crosslinker comprising an N-hydroxylsuccinimide ester group and a maleimide group linked via a polyethylene oxide spacer;

(b) removing excess heterobifunctional crosslinker; and (c) incubating the reaction product of step (b) with said allergen or autoantigen, wherein said allergen or autoantigen comprises at least one sulfhydryl group.

2. The method of claim 1, wherein said at least one sulfhydryl group of said allergen or autoantigen is introduced by:

(i) incubating said allergen or autoantigen in the presence of N-succinimidyl-S-acetylthioacetate (SATA);

(ii) removing excess SATA;

(iii) incubating the reaction product of step (ii) in the presence of hydroxylamine; and (iv) removing excess hydroxylamine and acetylated hydroxylamine.

3. The method of claim 1, wherein said heterobifunctional crosslinker comprising an N-hydroxylsuccinimide ester group and a maleimide group linked via a polyethylene oxide spacer has the formula:

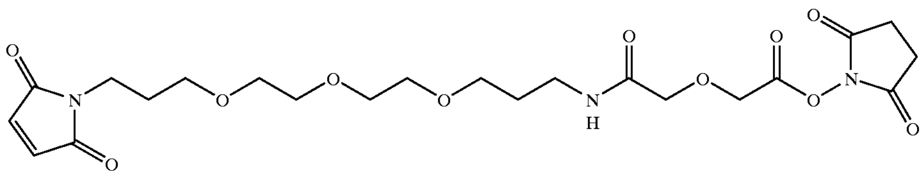

EXAMPLE 6

Influence of the amount of Amba-l used for crosslinking on the effectiveness of the conjugate The results in FIG. 6 show that 5 mg Amba-l was effective as far as the diminution or normalization of airway hyperresponsiveness is concerned (conjugate 3). In contrast, 2.5 mg was not (conjugate 4). Interestingly, for the same dose of Amba-l (5 mg) there was essentially no difference whether or not SATA was used before crosslinking (FIG. 6).

EXAMPLE 7

Effect of the conjugate on previously sensitized allergic animals

It was determined whether the conjugate is effective not only in naive but also in previously sensitized allergic animals. The protocol followed is shown in FIG. 7. The results with conjugates 6 and 7 clearly demonstrate that these conjugates downregulate sensitized mice.

EXAMPLE 8

Effect of the type of immunoglobulin used for conjugate synthesis

Monoclonal antibody with two different isotypes $\gamma_1$ and $\gamma_{2a}$ as the carrier molecule was tested, as compared to

4. The method of claim 1, wherein in step (a) the heterobifunctional crosslinker is used in a 5- to 50-fold higher molar concentration than said immunoglobulin or said structurally equivalent fragment thereof.

5. The method of claim 1, wherein steps (a) and (c) are performed in a temperature range from 20° C. to 37° C.

6. The method of claim 1, wherein steps (a) and (c) are performed in a time range from 30 min to 120 min.

7. The method of claim 1, wherein steps (a) and (c) are performed in a pH range from 7.0 to 9.0.

8. The method of claim 1, wherein the molar ratio of said immunoglobulin or said structurally equivalent fragment thereof compared to said allergen or autoantigen is between 1:1 and 1:10.

9. The method of claim 4, wherein steps (a) and (c) are performed in a buffer comprising 0.15 M borate, pH 8.0 at 37° C. for 30 min, the heterobifunctional crosslinker is used in a 30-fold higher molar concentration than said immunoglobulin or said structurally equivalent fragment thereof, and the molar ratio of said immunoglobulin or said struc turally equivalent fragment thereof compared to said allergen or autoantigen is 1:10.

10. The method of claim 1 further comprising the step of removing aggregated conjugate and providing the conjugate in monomeric form.

11. The method of claim 1, wherein said immunoglobulin or said structurally equivalent fragment thereof is an immunoglobulin G or a structurally equivalent fragment thereof.

12. The method of claim 1, wherein said allergen is derived from ragweed, birch pollen, peanut, house- dust mite, animal danders, or mould, or is tropomyosin.

13. The method of claim 1, wherein said autoantigen is acetylcholine receptor, insulin, insulin receptor, myelin basic protein.

* * * * *

UNITED STATES PATENT AND TRADEMARK OFFICE
CERTIFICATE OF CORRECTION

PATENT NO. : 6,537,519 B2
DATED : March 25, 2003
INVENTOR(S) : Yves Borel et al.

It is certified that error appears in the above-identified patent and that said Letters Patent is hereby corrected as shown below:

Column 10,
Line 62, "claim 4," should read -- claim 1, --.

Column 10, line 67 through Column 11, line 1,
"struc turally" should read -- structurally --.

Column 12,
Line 5, "receptor, myelin" should read -- receptor, or myelin --.

Signed and Sealed this

Eighteenth Day of November, 2003

JAMES E. ROGAN
*Director of the United States Patent and Trademark Office*